United States Patent [19]

Potter et al.

[11] Patent Number: 5,238,823
[45] Date of Patent: Aug. 24, 1993

[54] INTERLEUKIN-2-LEUKOTOXIN GENE FUSIONS AND USES THEREOF

[75] Inventors: Andrew Potter; Manuel Campos; Huw P. A. Hughes, all of Saskatoon, Canada

[73] Assignees: Veterinary Infectious Disease Organization, Saskatoon; Ciba-Geigy Canada td, Mississauga, both of Canada

[21] Appl. No.: 571,301

[22] Filed: Aug. 22, 1990

[51] Int. Cl.$^5$ .................... C12P 21/02; C07H 15/12
[52] U.S. Cl. .................. 435/69.52; 435/69.1; 435/69.3; 435/69.5; 435/69.7; 435/172.3; 435/320.1; 435/240.1; 435/243; 435/252.3; 536/23.4; 935/22; 935/24; 935/27; 935/47; 935/66
[58] Field of Search ............ 435/69.1, 69.3, 69.5, 435/69.52, 69.7, 172.3, 320.1, 243, 240.1, 252.3; 536/27; 935/22, 24, 27, 47, 66

[56] References Cited

U.S. PATENT DOCUMENTS

| 3,328,252 | 7/1967 | Mora | 424/92 |
|---|---|---|---|
| 4,167,560 | 9/1979 | Wohler, Jr. | 424/92 |
| 4,171,354 | 10/1979 | Smith | 424/92 |
| 4,328,210 | 5/1982 | Kucera | 424/92 |
| 4,346,074 | 8/1982 | Gilmour et al. | 424/92 |
| 4,675,382 | 6/1987 | Murphy | 530/350 |
| 4,818,769 | 4/1989 | Nunbey et al. | 514/12 |
| 4,933,288 | 6/1990 | Greenfield | 435/172.3 |
| 4,935,233 | 6/1990 | Bell et al. | 424/85.6 |
| 4,957,739 | 9/1990 | Berget et al. | 435/71.2 |
| 5,028,423 | 7/1991 | Prickett | 424/92 |
| 5,095,096 | 3/1992 | Miki et al. | 530/351 |

FOREIGN PATENT DOCUMENTS 0369316  5/1990  European Pat. Off.
WO8800971  2/1988  PCT Int'l Appl.

OTHER PUBLICATIONS

Conlon et al., *Infection and Immunity* (1991) 59(2):587–591.
Yates, *J. Can. Comp. Med.* (1982) 46:225–263.
Shewen et al., *Am. J. Vet. Res.* (1983) 44:715–719.
Donanchie et al., *J. Gen. Micro.* (1984) 130:1209–1216.
Martin et al., *Can. J. Comp. Med.* (1980) 44:1–10.
Shewen et al., *Can. J. Vet. Res.* (1988) 52:30–36.
Lessley et al., (1985) *Vet. Immunol. and Immunopathol.* (1985) 10:279–296.
Himmel et al., (1982) *Am. J. Vet. Res.* (1982) 43:764–767.
Gentry et al., *Vet. Immunol. and Immunopathol.* (1985) 9:239–250.
Strathdee et al., *Infect. Immunol.* (1987) 55:3233–3236.
Lo et al., *Infect. Immunol.* (1985) 50:667–671.
Cho et al., *Can. J. Vet. Res.* (1986) 50:27–31.
Cho et al., *Can. J. Comp. Med.* (1984) 48:151–155.
Lawman et al., "Recombinant Cytokines and their potential Therapeutic Value in Veterinary Medicine" in *Comprehensive Biotech, First Supplement, Animal Biotechnology* (1989) Pergamon Press, London, pp. 63–106.
Highlander et al., *DNA* (1989) 8(1):15–28.
Mosier et al., *infect. and Immunity* (1989) 57(3):711–716.
Strathdee et al., *J. Bacteriol.* (1989) 171(2):916–929.
Lorberboum-Galski et al, *PNAS* 85, 1988, pp. 1922–1926.
Williams et al, *Protein Engineering* vol. 1(6) 1987, pp. 493–498.
Lally et al, *Biochem Biophy Res Com* 159(1) 1989, pp. 256–262.
Lo et al, *Infect Immunity*, vol. 50(3), 1985, pp. 667–671.
Strathdee et al, *J. Barteriology*, 171(2), 189, pp. 916–929.

*Primary Examiner*—Garnette D. Draper
*Attorney, Agent, or Firm*—Reed & Robins

[57] ABSTRACT

New chimeric proteins, DNA encoding the same, and the use of these proteins in stimulating immunity against respiratory diseases such as pneumonia, including shipping fever pneumonia, are disclosed. The chimeric proteins include at least one epitope of leukotoxin fused to an active fragment of a cytokine. The chimeric proteins can be used in a vaccine composition. Also disclosed are methods of vaccination as well as methods of making the proteins employed in the vaccines.

14 Claims, 16 Drawing Sheets

GENETIC MAP OF PLASMIDS pAA356 CARRYING A BOVINE INTERLEUKIN-2::LEUKOTOXIN GENE FUSION tac = hybrid trp::lac promoter from E. coli
bla = beta lactamase gene (ampicillin resistance)
lktA = Pasteurella haemolytica leukotoxin structural gene
IL-2 = Bovine interleukin-2 structural gene
lacI = E. coli lac operon repressor The direction of transcription of the gene fusion is indicated by the arrow. The size of each component is not drawn to scale.

GENETIC MAP OF PLASMIDS pAA356 CARRYING A BOVINE INTERLEUKIN-2::LEUKOTOXIN GENE FUSION pAA356
~7780 BASE PAIRS tac
IL-2
lacI
bla
lktA

*tac* = hybrid *trp::lac* promoter from *E. coli*
*bla* = beta lactamase gene (ampicillin resistance)
*lktA* = *Pasteurella haemolytica* leukotoxin structural gene
*IL-2* = Bovine interleukin-2 structural gene
*lacI* = *E. coli lac* operon repressor The direction of transcription of the gene fusion is indicated by the arrow. The size of each component is not drawn to scale.

Figure 2

```
         10              20              30              40
          *               *               *               *
  *       *       *       *       *       *       *       *
ATG GCT ACT GTT AAT AGA TCT GCA CCT ACT TCA AGC TCT ACG GGG AAC
TAC CGA TGA CAA TTA TCT AGA CGT GGA TGA AGT TCG AGA TGC CCC TTG
Met Ala Thr Val Asn Arg Ser Ala Pro Thr Ser Ser Ser Thr Gly Asn>
___a___a___a___a___a____FUSION PROTEIN_a___a___a___a___a___a___>

50              60              70              80              90
  *               *               *               *               *
  *       *       *       *       *       *       *       *       *
ACA ATG AAA GAA GTG AAG TCA TTG CTG CTG GAT TTA CAG TTG CTT TTG
TGT TAC TTT CTT CAC TTC AGT AAC GAC GAC CTA AAT GTC AAC GAA AAC
Thr Met Lys Glu Val Lys Ser Leu Leu Leu Asp Leu Gln Leu Leu Leu>
___a___a___a___a___a____FUSION PROTEIN_a___a___a___a___a___a___>

100             110             120             130             140
  *               *               *               *               *
  *       *       *       *       *       *       *       *       *
GAG AAA GTT AAA AAT CCT GAG AAC CTC AAG CTC TCC AGG ATG CAT ACA
CTC TTT CAA TTT TTA GGA CTC TTG GAG TTC GAG AGG TCC TAC GTA TGT
Glu Lys Val Lys Asn Pro Glu Asn Leu Lys Leu Ser Arg Met His Thr>
___a___a___a___a___a____FUSION PROTEIN_a___a___a___a___a___a___>

150             160             170             180             190
        *               *               *               *               *
  *       *       *       *       *       *       *       *       *
TTT GAC TTT TAC GTG CCC AAG GTT AAC GCT ACA GAA TTG AAA CAT CTT
AAA CTG AAA ATG CAC GGG TTC CAA TTG CGA TGT CTT AAC TTT GTA GAA
Phe Asp Phe Tyr Val Pro Lys Val Asn Ala Thr Glu Leu Lys His Leu>
___a___a___a___a___a____FUSION PROTEIN_a___a___a___a___a___a___>
```

Figure 3A

```
           200         210         220         230         240
            *           *           *           *           *
AAG TGT TTA CTA GAA GAA CTC AAA CTT CTA GAG GAA GTG CTA AAT TTA
TTC ACA AAT GAT CTT CTT GAG TTT GAA GAT CTC CTT CAC GAT TTA AAT
Lys Cys Leu Leu Glu Glu Leu Lys Leu Leu Glu Glu Val Leu Asn Leu>
___a___a___a___a___a____FUSION PROTEIN_a___a___a___a___a___a___>

250         260         270         280
            *           *           *           *
GCT CCA AGC AAA AAC CTG AAC CCC AGA GAG ATC AAG GAT TCA ATG GAC
CGA GGT TCG TTT TTG GAC TTG GGG TCT CTC TAG TTC CTA AGT TAC CTG
Ala Pro Ser Lys Asn Leu Asn Pro Arg Glu Ile Lys Asp Ser Met Asp>
___a___a___a___a___a____FUSION PROTEIN_a___a___a___a___a___a___>

290         300         310         320         330
  *           *           *           *           *
AAT ATC AAG AGA ATC GTT TTG GAA CTA CAG GGA TCT GAA ACA AGA TTC
TTA TAG TTC TCT TAG CAA AAC CTT GAT GTC CCT AGA CTT TGT TCT AAG
Asn Ile Lys Arg Ile Val Leu Glu Leu Gln Gly Ser Glu Thr Arg Phe>
___a___a___a___a___a____FUSION PROTEIN_a___a___a___a___a___a___>

340         350         360         370         380
        *           *           *           *           *
ACA TGT GAA TAT GAT GAT GCA ACA GTA AAC GCT GTA GAA TTT CTG AAC
TGT ACA CTT ATA CTA CTA CGT TGT CAT TTG CGA CAT CTT AAA GAC TTG
Thr Cys Glu Tyr Asp Asp Ala Thr Val Asn Ala Val Glu Phe Leu Asn>
___a___a___a___a___a____FUSION PROTEIN_a___a___a___a___a___a___>

390         400         410         420         430
        *           *           *           *           *
AAA TGG ATT ACC TTT TGT CAA AGC ATC TAC TCA ACA ATG ACT GGG GAT
TTT ACC TAA TGG AAA ACA GTT TCG TAG ATG AGT TGT TAC TGA CCC CTA
Lys Trp Ile Thr Phe Cys Gln Ser Ile Tyr Ser Thr Met Thr Gly Asp>
___a___a___a___a___a____FUSION PROTEIN_a___a___a___a___a___a___>

440         450         460         470         480
          *           *           *           *           *
CTA AGC TTC CCT AGA CTT ACA ACC CTA TCA AAT GGG CTA AAA AAC ACT
GAT TCG AAG GGA TCT GAA TGT TGG GAT AGT TTA CCC GAT TTT TTG TGA
Leu Ser Phe Pro Arg Leu Thr Thr Leu Ser Asn Gly Leu Lys Asn Thr>
___a___a___a___a___a____FUSION PROTEIN_a___a___a___a___a___a___>

490         500         510         520
           *           *           *           *
TTA ACG GCA ACC AAA AGT GGC TTA CAT AAA GCC GGT CAA TCA TTA ACC
AAT TGC CGT TGG TTT TCA CCG AAT GTA TTT CGG CCA GTT AGT AAT TGG
Leu Thr Ala Thr Lys Ser Gly Leu His Lys Ala Gly Gln Ser Leu Thr>
___a___a___a___a___a____FUSION PROTEIN_a___a___a___a___a___a___>
```

Figure 3B

```
     530         540         550         560         570
      *           *           *           *           *
   *           *           *           *           *
CAA GCC GGC AGT TCT TTA AAA ACT GGG GCA AAA AAA ATT ATC CTC TAT
GTT CGG CCG TCA AGA AAT TTT TGA CCC CGT TTT TTT TAA TAG GAG ATA
Gln Ala Gly Ser Ser Leu Lys Thr Gly Ala Lys Lys Ile Ile Leu Tyr>
___a___a___a___a___a____FUSION PROTEIN_a___a___a___a___a___a___>

580         590         600         610         620
      *           *           *           *           *
   *           *           *           *           *
ATT CCC CAA AAT TAC CAA TAT GAT ACT GAA CAA GGT AAT GGT TTA CAG
TAA GGG GTT TTA ATG GTT ATA CTA TGA CTT GTT CCA TTA CCA AAT GTC
Ile Pro Gln Asn Tyr Gln Tyr Asp Thr Glu Gln Gly Asn Gly Leu Gln>
___a___a___a___a___a____FUSION PROTEIN_a___a___a___a___a___a___>

630         640         650         660         670
   *    *     *     *     *    *     *     *    *     *
GAT TTA GTC AAA GCG GCC GAA GAG TTG GGG ATT GAG GTA CAA AGA GAA
CTA AAT CAG TTT CGC CGG CTT CTC AAC CCC TAA CTC CAT GTT TCT CTT
Asp Leu Val Lys Ala Ala Glu Glu Leu Gly Ile Glu Val Gln Arg Glu>
___a___a___a___a___a____FUSION PROTEIN_a___a___a___a___a___a___>

680         690         700         710         720
      *           *           *           *           *
   *           *           *           *           *
GAA CGC AAT AAT ATT GCA ACA GCT CAA ACC AGT TTA GGC ACG ATT CAA
CTT GCG TTA TTA TAA CGT TGT CGA GTT TGG TCA AAT CCG TGC TAA GTT
Glu Arg Asn Asn Ile Ala Thr Ala Gln Thr Ser Leu Gly Thr Ile Gln>
___a___a___a___a___a____FUSION PROTEIN_a___a___a___a___a___a___>

730         740         750         760
   *    *     *     *     *    *     *     *    *
ACC GCT ATT GGC TTA ACT GAG CGT GGC ATT GTG TTA TCC GCT CCA CAA
TGG CGA TAA CCG AAT TGA CTC GCA CCG TAA CAC AAT AGG CGA GGT GTT
Thr Ala Ile Gly Leu Thr Glu Arg Gly Ile Val Leu Ser Ala Pro Gln>
___a___a___a___a___a____FUSION PROTEIN_a___a___a___a___a___a___>

770         780         790         800         810
    *           *           *           *           *
 *           *           *           *           *
ATT GAT AAA TTG CTA CAG AAA ACT AAA GCA GGC CAA GCA TTA GGT TCT
TAA CTA TTT AAC GAT GTC TTT TGA TTT CGT CCG GTT CGT AAT CCA AGA
Ile Asp Lys Leu Leu Gln Lys Thr Lys Ala Gly Gln Ala Leu Gly Ser>
___a___a___a___a___a____FUSION PROTEIN_a___a___a___a___a___a___>
```

Figure 3C

```
           820           830           840           850           860
            *             *             *             *             *
       *         *             *   *         *             *     *
   GCC GAA AGC ATT GTA CAA AAT GCA AAT AAA GCC AAA ACT GTA TTA TCT
   CGG CTT TCG TAA CAT GTT TTA CGT TTA TTT CGG TTT TGA CAT AAT AGA
   Ala Glu Ser Ile Val Gln Asn Ala Asn Lys Ala Lys Thr Val Leu Ser>
   ___a___a___a___a___a____FUSION PROTEIN_a___a___a___a___a___a___>

870           880           890           900           910
            *             *             *             *             *
       *         *     *         *             *         *     *
   GGC ATT CAA TCT ATT TTA GGC TCA GTA TTG GCT GGA ATG GAT TTA GAT
   CCG TAA GTT AGA TAA AAT CCG AGT CAT AAC CGA CCT TAC CTA AAT CTA
   Gly Ile Gln Ser Ile Leu Gly Ser Val Leu Ala Gly Met Asp Leu Asp>
   ___a___a___a___a___a____FUSION PROTEIN_a___a___a___a___a___a___>

920           930           940           950           960
            *             *             *             *             *
       *         *     *         *             *         *     *
   GAG GCC TTA CAG AAT AAC AGC AAC CAA CAT GCT CTT GCT AAA GCT GGC
   CTC CGG AAT GTC TTA TTG TCG TTG GTT GTA CGA GAA CGA TTT CGA CCG
   Glu Ala Leu Gln Asn Asn Ser Asn Gln His Ala Leu Ala Lys Ala Gly>
   ___a___a___a___a___a____FUSION PROTEIN_a___a___a___a___a___a___>

970           980           990          1000
                  *             *             *             *
            *           *             *             *           *
       TTG GAG CTA ACA AAT TCA TTA ATT GAA AAT ATT GCT AAT TCA GTA AAA
       AAC CTC GAT TGT TTA AGT AAT TAA CTT TTA TAA CGA TTA AGT CAT TTT
       Leu Glu Leu Thr Asn Ser Leu Ile Glu Asn Ile Ala Asn Ser Val Lys>
       ___a___a___a___a___a____FUSION PROTEIN_a___a___a___a___a___a___>

1010          1020          1030          1040          1050
      *             *             *             *             *
            *             *       *         *             *         *
   ACA CTT GAC GAA TTT GGT GAG CAA ATT AGT CAA TTT GGT TCA AAA CTA
   TGT GAA CTG CTT AAA CCA CTC GTT TAA TCA GTT AAA CCA AGT TTT GAT
   Thr Leu Asp Glu Phe Gly Glu Gln Ile Ser Gln Phe Gly Ser Lys Leu>
   ___a___a___a___a___a____FUSION PROTEIN_a___a___a___a___a___a___>

1060          1070          1080          1090          1100
          *             *             *             *             *
               *             *             *             *         *
   CAA AAT ATC AAA GGC TTA GGG ACT TTA GGA GAC AAA CTC AAA AAT ATC
   GTT TTA TAG TTT CCG AAT CCC TGA AAT CCT CTG TTT GAG TTT TTA TAG
   Gln Asn Ile Lys Gly Leu Gly Thr Leu Gly Asp Lys Leu Lys Asn Ile>
   ___a___a___a___a___a____FUSION PROTEIN_a___a___a___a___a___a___>

1110          1120          1130          1140          1150
          *             *             *             *             *
               *             *             *             *         *
   GGT GGA CTT GAT AAA GCT GGC CTT GGT TTA GAT GTT ATC TCA GGG CTA
   CCA CCT GAA CTA TTT CGA CCG GAA CCA AAT CTA CAA TAG AGT CCC GAT
   Gly Gly Leu Asp Lys Ala Gly Leu Gly Leu Asp Val Ile Ser Gly Leu>
   ___a___a___a___a___a____FUSION PROTEIN_a___a___a___a___a___a___>
```

Figure 3D

```
        1160            1170            1180            1190            1200
 *        *      *        *      *        *      *        *      *        *
TTA TCG GGC GCA ACA GCT GCA CTT GTA CTT GCA GAT AAA AAT GCT TCA
AAT AGC CCG CGT TGT CGA CGT GAA CAT GAA CGT CTA TTT TTA CGA AGT
Leu Ser Gly Ala Thr Ala Ala Leu Val Leu Ala Asp Lys Asn Ala Ser>
___a___a___a___a___a____FUSION PROTEIN_a___a___a___a___a___a___>

1210            1220            1230            1240
 *        *      *        *      *        *      *        *
ACA GCT AAA AAA GTG GGT GCG GGT TTT GAA TTG GCA AAC CAA GTT GTT
TGT CGA TTT TTT CAC CCA CGC CCA AAA CTT AAC CGT TTG GTT CAA CAA
Thr Ala Lys Lys Val Gly Ala Gly Phe Glu Leu Ala Asn Gln Val Val>
___a___a___a___a___a____FUSION PROTEIN_a___a___a___a___a___a___>

1250          1260            1270            1280            1290
 *      *      *      *        *      *      *        *      *        *
GGT AAT ATT ACC AAA GCC GTT TCT TCT TAC ATT TTA GCC CAA CGT GTT
CCA TTA TAA TGG TTT CGG CAA AGA AGA ATG TAA AAT CGG GTT GCA CAA
Gly Asn Ile Thr Lys Ala Val Ser Ser Tyr Ile Leu Ala Gln Arg Val>
___a___a___a___a___a____FUSION PROTEIN_a___a___a___a___a___a___>

1300           1310            1320            1330            1340
 *       *      *      *        *      *      *        *      *        *
GCA GCA GGT TTA TCT TCA ACT GGG CCT GTG GCT GCT TTA ATT GCT TCT
CGT CGT CCA AAT AGA AGT TGA CCC GGA CAC CGA CGA AAT TAA CGA AGA
Ala Ala Gly Leu Ser Ser Thr Gly Pro Val Ala Ala Leu Ile Ala Ser>
___a___a___a___a___a____FUSION PROTEIN_a___a___a___a___a___a___>

1350            1360            1370            1380            1390
 *        *      *        *      *        *      *        *      *        *
ACT GTT TCT CTT GCG ATT AGC CCA TTA GCA TTT GCC GGT ATT GCC GAT
TGA CAA AGA GAA CGC TAA TCG GGT AAT CGT AAA CGG CCA TAA CGG CTA
Thr Val Ser Leu Ala Ile Ser Pro Leu Ala Phe Ala Gly Ile Ala Asp>
___a___a___a___a___a____FUSION PROTEIN_a___a___a___a___a___a___>

1400            1410            1420            1430            1440
 *        *      *        *      *        *      *        *      *        *
AAA TTT AAT CAT GCA AAA AGT TTA GAG AGT TAT GCC GAA CGC TTT AAA
TTT AAA TTA GTA CGT TTT TCA AAT CTC TCA ATA CGG CTT GCG AAA TTT
Lys Phe Asn His Ala Lys Ser Leu Glu Ser Tyr Ala Glu Arg Phe Lys>
___a___a___a___a___a____FUSION PROTEIN_a___a___a___a___a___a___>
```

Figure 3E

```
          1450           1460          1470          1480
    *      *      *      *     *      *      *      *     *
   AAA    TTA    GGC    TAT   GAC    GGA    GAT    AAT   TTA    TTA    GCA    GAA    TAT   CAG    CGG    GGA
   TTT    AAT    CCG    ATA   CTG    CCT    CTA    TTA   AAT    AAT    CGT    CTT    ATA   GTC    GCC    CCT
   Lys    Leu    Gly    Tyr   Asp    Gly    Asp    Asn   Leu    Leu    Ala    Glu    Tyr   Gln    Arg    Gly>
   ___a___a___a___a___a____FUSION PROTEIN_a___a___a___a___a___a___>

1490          1500          1510          1520          1530
    *      *      *      *     *      *      *      *     *      *
   ACA    GGG    ACT    ATT   GAT    GCA    TCG    GTT   ACT    GCA    ATT    AAT    ACC   GCA    TTG    GCC
   TGT    CCC    TGA    TAA   CTA    CGT    AGC    CAA   TGA    CGT    TAA    TTA    TGG   CGT    AAC    CGG
   Thr    Gly    Thr    Ile   Asp    Ala    Ser    Val   Thr    Ala    Ile    Asn    Thr   Ala    Leu    Ala>
   ___a___a___a___a___a____FUSION PROTEIN_a___a___a___a___a___a___>

1540          1550          1560          1570          1580
    *      *      *     *      *      *      *      *     *      *
   GCT    ATT    GCT    GGT   GGT    GTG    TCT    GCT   GCT    GCA    GCC    GGC    TCG   GTT    ATT    GCT
   CGA    TAA    CGA    CCA   CCA    CAC    AGA    CGA   CGA    CGT    CGG    CCG    AGC   CAA    TAA    CGA
   Ala    Ile    Ala    Gly   Gly    Val    Ser    Ala   Ala    Ala    Ala    Gly    Ser   Val    Ile    Ala>
   ___a___a___a___a___a____FUSION PROTEIN_a___a___a___a___a___a___>

1590          1600          1610          1620          1630
    *      *      *     *      *      *      *      *     *      *
   TCA    CCG    ATT    GCC   TTA    TTA    GTA    TCT   GGG    ATT    ACC    GGT    GTA   ATT    TCT    ACG
   AGT    GGC    TAA    CGG   AAT    AAT    CAT    AGA   CCC    TAA    TGG    CCA    CAT   TAA    AGA    TGC
   Ser    Pro    Ile    Ala   Leu    Leu    Val    Ser   Gly    Ile    Thr    Gly    Val   Ile    Ser    Thr>
   ___a___a___a___a___a____FUSION PROTEIN_a___a___a___a___a___a___>

1640          1650          1660          1670          1680
    *      *      *     *      *      *      *      *     *      *
   ATT    CTG    CAA    TAT   TCT    AAA    CAA    GCA   ATG    TTT    GAG    CAC    GTT   GCA    AAT    AAA
   TAA    GAC    GTT    ATA   AGA    TTT    GTT    CGT   TAC    AAA    CTC    GTG    CAA   CGT    TTA    TTT
   Ile    Leu    Gln    Tyr   Ser    Lys    Gln    Ala   Met    Phe    Glu    His    Val   Ala    Asn    Lys>
   ___a___a___a___a___a____FUSION PROTEIN_a___a___a___a___a___a___>

1690          1700          1710          1720
    *      *      *     *      *      *      *      *     *
   ATT    CAT    AAC    AAA   ATT    GTA    GAA    TGG   GAA    AAA    AAT    AAT    CAC   GGT    AAG    AAC
   TAA    GTA    TTG    TTT   TAA    CAT    CTT    ACC   CTT    TTT    TTA    TTA    GTG   CCA    TTC    TTG
   Ile    His    Asn    Lys   Ile    Val    Glu    Trp   Glu    Lys    Asn    Asn    His   Gly    Lys    Asn>
   ___a___a___a___a___a____FUSION PROTEIN_a___a___a___a___a___a___>

1730          1740          1750          1760          1770
    *      *     *      *      *      *      *      *     *      *
   TAC    TTT    GAA    AAT   GGT    TAC    GAT    GCC   CGT    TAT    CTT    GCG    AAT   TTA    CAA    GAT
   ATG    AAA    CTT    TTA   CCA    ATG    CTA    CGG   GCA    ATA    GAA    CGC    TTA   AAT    GTT    CTA
   Tyr    Phe    Glu    Asn   Gly    Tyr    Asp    Ala   Arg    Tyr    Leu    Ala    Asn   Leu    Gln    Asp>
   ___a___a___a___a___a____FUSION PROTEIN_a___a___a___a___a___a___>
```

Figure 3F

```
      1780          1790          1800          1810          1820
        *             *             *             *             *
   AAT ATG AAA TTC TTA CTG AAC TTA AAC AAA GAG TTA CAG GCA GAA CGT
   TTA TAC TTT AAG AAT GAC TTG AAT TTG TTT CTC AAT GTC CGT CTT GCA
   Asn Met Lys Phe Leu Leu Asn Leu Asn Lys Glu Leu Gln Ala Glu Arg>
   ___a___a___a___a___a____FUSION PROTEIN_a___a___a___a___a___a___>

1830          1840          1850          1860          1870
        *             *             *             *             *
   GTC ATC GCT ATT ACT CAG CAG CAA TGG GAT AAC AAC ATT GGT GAT TTA
   CAG TAG CGA TAA TGA GTC GTC GTT ACC CTA TTG TTG TAA CCA CTA AAT
   Val Ile Ala Ile Thr Gln Gln Gln Trp Asp Asn Asn Ile Gly Asp Leu>
   ___a___a___a___a___a____FUSION PROTEIN_a___a___a___a___a___a___>

1880          1890          1900          1910          1920
        *             *             *             *             *
   GCT GGT ATT AGC CGT TTA GGT GAA AAA GTC CTT AGT GGT AAA GCC TAT
   CGA CCA TAA TCG GCA AAT CCA CTT TTT CAG GAA TCA CCA TTT CGG ATA
   Ala Gly Ile Ser Arg Leu Gly Glu Lys Val Leu Ser Gly Lys Ala Tyr>
   ___a___a___a___a___a____FUSION PROTEIN_a___a___a___a___a___a___>

1930          1940          1950          1960
        *             *             *             *
   GTG GAT GCG TTT GAA GAA GGC AAA CAC ATT AAA GCC GAT AAA TTA GTA
   CAC CTA CGC AAA CTT CTT CCG TTT GTG TAA TTT CGG CTA TTT AAT CAT
   Val Asp Ala Phe Glu Glu Gly Lys His Ile Lys Ala Asp Lys Leu Val>
   ___a___a___a___a___a____FUSION PROTEIN_a___a___a___a___a___a___>

1970          1980          1990          2000          2010
   *             *             *             *             *
   CAG TTG GAT TCG GCA AAC GGT ATT ATT GAT GTG AGT AAT TCG GGT AAA
   GTC AAC CTA AGC CGT TTG CCA TAA TAA CTA CAC TCA TTA AGC CCA TTT
   Gln Leu Asp Ser Ala Asn Gly Ile Ile Asp Val Ser Asn Ser Gly Lys>
   ___a___a___a___a___a____FUSION PROTEIN_a___a___a___a___a___a___>

2020          2030          2040          2050          2060
    *             *             *             *             *
   GCG AAA ACT CAG CAT ATC TTA TTC AGA ACG CCA TTA TTG ACG CCG GGA
   CGC TTT TGA GTC GTA TAG AAT AAG TCT TGC GGT AAT AAC TGC GGC CCT
   Ala Lys Thr Gln His Ile Leu Phe Arg Thr Pro Leu Leu Thr Pro Gly>
   ___a___a___a___a___a____FUSION PROTEIN_a___a___a___a___a___a___>
```

Figure 3G

```
           2070         2080         2090         2100         2110
        *    *       *    *       *    *       *    *       *    *
   ACA GAG CAT CGT GAA CGC GTA CAA ACA GGT AAA TAT GAA TAT ATT ACC
   TGT CTC GTA GCA CTT GCG CAT GTT TGT CCA TTT ATA CTT ATA TAA TGG
   Thr Glu His Arg Glu Arg Val Gln Thr Gly Lys Tyr Glu Tyr Ile Thr>
   ___a___a___a___a___a___FUSION PROTEIN_a___a___a___a___a___a___>

2120         2130         2140         2150         2160
           *    *       *    *       *    *       *    *       *    *
      AAG CTC AAT ATT AAC CGT GTA GAT AGC TGG AAA ATT ACA GAT GGT GCA
      TTC GAG TTA TAA TTG GCA CAT CTA TCG ACC TTT TAA TGT CTA CCA CGT
      Lys Leu Asn Ile Asn Arg Val Asp Ser Trp Lys Ile Thr Asp Gly Ala>
      ___a___a___a___a___a___FUSION PROTEIN_a___a___a___a___a___a___>

2170         2180         2190         2200
           *    *       *    *       *    *       *    *       *
   GCA AGT TCT ACC TTT GAT TTA ACT AAC GTT GTT CAG CGT ATT GGT ATT
   CGT TCA AGA TGG AAA CTA AAT TGA TTG CAA CAA GTC GCA TAA CCA TAA
   Ala Ser Ser Thr Phe Asp Leu Thr Asn Val Val Gln Arg Ile Gly Ile>
   ___a___a___a___a___a___FUSION PROTEIN_a___a___a___a___a___a___>

2210         2220         2230         2240         2250
   *    *       *    *       *    *       *    *       *    *
 GAA TTA GAC AAT GCT GGA AAT GTA ACT AAA ACC AAA GAA ACA AAA ATT
 CTT AAT CTG TTA CGA CCT TTA CAT TGA TTT TGG TTT CTT TGT TTT TAA
 Glu Leu Asp Asn Ala Gly Asn Val Thr Lys Thr Lys Glu Thr Lys Ile>
 ___a___a___a___a___a___FUSION PROTEIN_a___a___a___a___a___a___>

2260         2270         2280         2290         2300
     *    *       *    *       *    *       *    *       *    *
   ATT GCC AAA CTT GGT GAA GGT GAT GAC AAC GTA TTT GTT GGT TCT GGT
   TAA CGG TTT GAA CCA CTT CCA CTA CTG TTG CAT AAA CAA CCA AGA CCA
   Ile Ala Lys Leu Gly Glu Gly Asp Asp Asn Val Phe Val Gly Ser Gly>
   ___a___a___a___a___a___FUSION PROTEIN_a___a___a___a___a___a___>

2310         2320         2330         2340         2350
        *    *       *    *       *    *       *    *       *    *
   ACG ACG GAA ATT GAT GGC GGT GAA GGT TAC GAC CGA GTT CAC TAT AGC
   TGC TGC CTT TAA CTA CCG CCA CTT CCA ATG CTG GCT CAA GTG ATA TCG
   Thr Thr Glu Ile Asp Gly Gly Glu Gly Tyr Asp Arg Val His Tyr Ser>
   ___a___a___a___a___a___FUSION PROTEIN_a___a___a___a___a___a___>

2360         2370         2380         2390         2400
           *    *       *    *       *    *       *    *       *    *
   CGT GGA AAC TAT GGT GCT TTA ACT ATT GAT GCA ACC AAA GAG ACC GAG
   GCA CCT TTG ATA CCA CGA AAT TGA TAA CTA CGT TGG TTT CTC TGG CTC
   Arg Gly Asn Tyr Gly Ala Leu Thr Ile Asp Ala Thr Lys Glu Thr Glu>
   ___a___a___a___a___a___FUSION PROTEIN_a___a___a___a___a___a___>
```

Figure 3H

```
         2410            2420            2430            2440
          *               *               *               *
    *         *       *         *      *        *      *         *
CAA GGT AGT TAT ACC GTA AAT CGT TTC GTA GAA ACC GGT AAA GCA CTA
GTT CCA TCA ATA TGG CAT TTA GCA AAG CAT CTT TGG CCA TTT CGT GAT
Gln Gly Ser Tyr Thr Val Asn Arg Phe Val Glu Thr Gly Lys Ala Leu>
___a___a___a___a___a____FUSION PROTEIN_a___a___a___a___a___a___>

2450            2460            2470            2480            2490
   *               *               *               *               *
*         *      *         *    *         *      *         *     *
CAC GAA GTG ACT TCA ACC CAT ACC GCA TTA GTG GGC AAC CGT GAA GAA
GTG CTT CAC TGA AGT TGG GTA TGG CGT AAT CAC CCG TTG GCA CTT CTT
His Glu Val Thr Ser Thr His Thr Ala Leu Val Gly Asn Arg Glu Glu>
___a___a___a___a___a____FUSION PROTEIN_a___a___a___a___a___a___>

2500           2510            2520           2530          · 2540
        *              *               *              *              *
     *       *      *        *      *        *     *        *     *
AAA ATA GAA TAT CGT CAT AGC AAT AAC CAG CAC CAT GCC GGT TAT TAC
TTT TAT CTT ATA GCA GTA TCG TTA TTG GTC GTG GTA CGG CCA ATA ATG
Lys Ile Glu Tyr Arg His Ser Asn Asn Gln His His Ala Gly Tyr Tyr>
___a___a___a___a___a____FUSION PROTEIN_a___a___a___a___a___a___>

2550            2560            2570            2580            2590
        *               *               *               *               *
   *         *      *         *     *        *      *         *      *
ACC AAA GAT ACC TTG AAA GCT GTT GAA GAA ATT ATC GGT ACA TCA CAT
TGG TTT CTA TGG AAC TTT CGA CAA CTT CTT TAA TAG CCA TGT AGT GTA
Thr Lys Asp Thr Leu Lys Ala Val Glu Glu Ile Ile Gly Thr Ser His>
___a___a___a___a___a____FUSION PROTEIN_a___a___a___a___a___a___>

2600            2610            2620            2630            2640
           *               *               *               *               *
        *         *      *        *      *        *      *        *      *
AAC GAT ATC TTT AAA GGT AGT AAG TTC AAT GAT GCC TTT AAC GGT GGT
TTG CTA TAG AAA TTT CCA TCA TTC AAG TTA CTA CGG AAA TTG CCA CCA
Asn Asp Ile Phe Lys Gly Ser Lys Phe Asn Asp Ala Phe Asn Gly Gly>
___a___a___a___a___a____FUSION PROTEIN_a___a___a___a___a___a___>

2650            2660            2670            2680
              *               *               *               *
          *         *     *         *      *         *      *
GAT GGT GTC GAT ACT ATT GAC GGT AAC GAC GGC AAT GAC CGC TTA TTT
CTA CCA CAG CTA TGA TAA CTG CCA TTG CTG CCG TTA CTG GCG AAT AAA
Asp Gly Val Asp Thr Ile Asp Gly Asn Asp Gly Asn Asp Arg Leu Phe>
___a___a___a___a___a____FUSION PROTEIN_a___a___a___a___a___a___>
```

Figure 31

```
      2690          2700          2710          2720          2730
       *      *      *      *      *      *      *      *      *      *
 GGT GGT AAA GGC GAT GAT ATT CTC GAT GGT GGA AAT GGT GAT GAT TTT
 CCA CCA TTT CCG CTA CTA TAA GAG CTA CCA CCT TTA CCA CTA CTA AAA
 Gly Gly Lys Gly Asp Asp Ile Leu Asp Gly Gly Asn Gly Asp Asp Phe>
 ___a___a___a___a___a___FUSION PROTEIN_a___a___a___a___a___a___>

2740          2750          2760          2770          2780
       *      *      *      *      *      *      *      *      *      *
 ATC GAT GGC GGT AAA GGC AAC GAC CTA TTA CAC GGT GGC AAG GGC GAT
 TAG CTA CCG CCA TTT CCG TTG CTG GAT AAT GTG CCA CCG TTC CCG CTA
 Ile Asp Gly Gly Lys Gly Asn Asp Leu Leu His Gly Gly Lys Gly Asp>
 ___a___a___a___a___a___FUSION PROTEIN_a___a___a___a___a___a___>

2790          2800          2810          2820          2830
       *      *      *      *      *      *      *      *      *      *
 GAT ATT TTC GTT CAC CGT AAA GGC GAT GGT AAT GAT ATT ATT ACC GAT
 CTA TAA AAG CAA GTG GCA TTT CCG CTA CCA TTA CTA TAA TAA TGG CTA
 Asp Ile Phe Val His Arg Lys Gly Asp Gly Asn Asp Ile Ile Thr Asp>
 ___a___a___a___a___a___FUSION PROTEIN_a___a___a___a___a___a___>

2840          2850          2860          2870          2880
           *      *      *      *      *      *      *      *      *      *
 TCT GAC GGC AAT GAT AAA TTA TCA TTC TCT GAT TCG AAC TTA AAA GAT
 AGA CTG CCG TTA CTA TTT AAT AGT AAG AGA CTA AGC TTG AAT TTT CTA
 Ser Asp Gly Asn Asp Lys Leu Ser Phe Ser Asp Ser Asn Leu Lys Asp>
 ___a___a___a___a___a___FUSION PROTEIN_a___a___a___a___a___a___>

2890          2900          2910          2920
            *      *      *      *      *      *      *      *      *
 TTA ACA TTT GAA AAA GTT AAA CAT AAT CTT GTC ATC ACG AAT AGC AAA
 AAT TGT AAA CTT TTT CAA TTT GTA TTA GAA CAG TAG TGC TTA TCG TTT
 Leu Thr Phe Glu Lys Val Lys His Asn Leu Val Ile Thr Asn Ser Lys>
 ___a___a___a___a___a___FUSION PROTEIN_a___a___a___a___a___a___>

2930          2940          2950          2960          2970
    *      *      *      *      *      *      *      *      *      *
 AAA GAG AAA GTG ACC ATT CAA AAC TGG TTC CGA GAG GCT GAT TTT GCT
 TTT CTC TTT CAC TGG TAA GTT TTG ACC AAG GCT CTC CGA CTA AAA CGA
 Lys Glu Lys Val Thr Ile Gln Asn Trp Phe Arg Glu Ala Asp Phe Ala>
 ___a___a___a___a___a___FUSION PROTEIN_a___a___a___a___a___a___>

2980          2990          3000          3010          3020
        *      *      *      *      *      *      *      *      *      *
 AAA GAA GTG CCT AAT TAT AAA GCA ACT AAA GAT GAG AAA ATC GAA GAA
 TTT CTT CAC GGA TTA ATA TTT CGT TGA TTT CTA CTC TTT TAG CTT CTT
 Lys Glu Val Pro Asn Tyr Lys Ala Thr Lys Asp Glu Lys Ile Glu Glu>
 ___a___a___a___a___a___FUSION PROTEIN_a___a___a___a___a___a___>
```

Figure 3J

```
         3030           3040           3050           3060           3070
  *       *       *      *       *      *       *      *       *      *
ATC ATC GGT CAA AAT GGC GAG CGG ATC ACC TCA AAG CAA GTT GAT GAT
TAG TAG CCA GTT TTA CCG CTC GCC TAG TGG AGT TTC GTT CAA CTA CTA
Ile Ile Gly Gln Asn Gly Glu Arg Ile Thr Ser Lys Gln Val Asp Asp>
___a___a___a___a___a_____FUSION PROTEIN_a___a___a___a___a___a___>

3080           3090          3100           3110          3120
  *       *      *       *      *      *       *      *      *     *
CTT ATC GCA AAA GGT AAC GGC AAA ATT ACC CAA GAT GAG CTA TCA AAA
GAA TAG CGT TTT CCA TTG CCG TTT TAA TGG GTT CTA CTC GAT AGT TTT
Leu Ile Ala Lys Gly Asn Gly Lys Ile Thr Gln Asp Glu Leu Ser Lys>
___a___a___a___a___a_____FUSION PROTEIN_a___a___a___a___a___a___>

3130           3140          3150           3160
  *       *      *       *      *      *       *      *       *
GTT GTT GAT AAC TAT GAA TTG CTC AAA CAT AGC AAA AAT GTG ACA AAC
CAA CAA CTA TTG ATA CTT AAC GAG TTT GTA TCG TTT TTA CAC TGT TTG
Val Val Asp Asn Tyr Glu Leu Leu Lys His Ser Lys Asn Val Thr Asn>
___a___a___a___a___a_____FUSION PROTEIN_a___a___a___a___a___a____>

3170           3180           3190           3200          3210
  *      *       *      *       *      *       *      *     *    *
AGC TTA GAT AAG TTA ATC TCA TCT GTA AGT GCA TTT ACC TCG TCT AAT
TCG AAT CTA TTC AAT TAG AGT AGA CAT TCA CGT AAA TGG AGC AGA TTA
Ser Leu Asp Lys Leu Ile Ser Ser Val Ser Ala Phe Thr Ser Ser Asn>
___a___a___a___a___a_____FUSION PROTEIN_a___a___a___a___a___a___>

3220           3230          3240           3250           3260
  *      *      *     *       *      *       *      *       *     *
GAT TCG AGA AAT GTA TTA GTG GCT CCA ACT TCA ATG TTG GAT CAA AGT
CTA AGC TCT TTA CAT AAT CAC CGA GGT TGA AGT TAC AAC CTA GTT TCA
Asp Ser Arg Asn Val Leu Val Ala Pro Thr Ser Met Leu Asp Gln Ser>
___a___a___a___a___a_____FUSION PROTEIN_a___a___a___a___a___a___>

3270         3280            3290          3300       3310
  *       *      *      *      *     *       *      *      *       *
TTA TCT TCT CTT CAA TTT GCT AGG GGA TCC TAG CTAGCTAGCCATGG
AAT AGA AGA GAA GTT AAA CGA TCC CCT AGG ATC GATCGATCGGTACC
Leu Ser Ser Leu Gln Phe Ala Arg Gly Ser End>
___a___a___a__FUSION PROTEIN___a___a___a___>
```

Figure 3K

INTERLEUKIN-2-LEUKOTOXIN GENE FUSIONS AND USES THEREOF

DESCRIPTION

1. Technical Field

The present invention relates generally to subunit antigens, vaccine compositions, and methods of administering the same. More particularly, the present invention relates to an interleukin-2-leukotoxin gene fusion product and the use of the same for stimulating immunity against pneumonia.

2. Background of the Invention

Respiratory disease affecting feedlot cattle causes tremendous losses yearly to the cattle industry. Calves are the most severely affected, and a large number of these calves die. This disease is associated with pathogenic microorganisms, particularly Pasteurallae species, and various stresses, such as transportation and overcrowding.

Shipping fever is the most economically important respiratory disease associated with Pasteurella species. The disease is characterized by sudden onset, usually within two weeks of stress. The symptoms include dyspnea, cough, ocular and nasal discharge, inappetence and rapid weight loss, fever, increased lung sounds, immunosuppression, general depression, viral and/or bacterial infection of the lungs. Various bacteria and viruses have been isolated from affected animals including Pasteurella spp., bovine herpes virus 1, parainfluenza-3 virus, bovine respiratory syncytial virus and Mycoplasma species. The disease typically affects 15–30% of exposed animals and the resulting deaths are typically 2–5% of the exposed population.

Exposure of the animal to stress, plus infection with a variety of viruses, as described above, appears to make the animal susceptible to fibrinous pneumonia caused by *P. haemolytica*, and to a lesser extent, *Pasteurella multocida*. For a general background on shipping fever see Yates, W. D. G. (1982) *Can. J. Comp. Med.* 46:225–263.

*P. haemolytica* also causes enzootic pneumonia and can infect a wide range of animals, in addition to cattle, including economically important species such as sheep, swine, horses and fowl. *P. haemolytica* is also frequently found in the upper respiratory tract of healthy animals. Pneumonia develops when the bacteria infects the lungs of these animals. Protection against Pasteurella-associated diseases is therefore economically important to the agricultural industry.

There are two known biotypes of *P. haemolytica* designated A and T. There are also 12 recognized serotypes which have been isolated from ruminants. Biotype A, serotype 1 (referred to hereinafter as "A1") predominates in bovine pneumonia in North America. Shewen, P. E., and Wilkie, B. N. (1983) *Am. J. Vet. Res.* 44:715–719. However, antigens isolated from different serotypes appear to be somewhat cross-reactive. See, e.g., Donanchie et al. (1984) *J. Gen. Micro.* 130:1209–1216.

Previous Pasteurellosis vaccines have utilized whole cell preparations of either live or heat killed bacteria of various serotypes as described in U.S. Pat. Nos. 4,328,210, 4,171,354, 3,328,252, 4,167,560 and 4,346,074. Traditional vaccine preparations, however, have not been effective in protecting against Pasteurella infections. Indeed, vaccinated animals are frequently more susceptible to the disease than their non-vaccinated counterparts. Martin et al. (1980) *Can. J. Comp. Med.* 44:1–10. The lack of protection offered by traditional vaccines is probably due to the absence of important antigens, virulence determinants, or the presence of immunosuppressive components in the preparations, Other vaccine preparations have included crude supernatant extracts from *P. haemolytica*. See, e.g., Shewen, P. E., and Wilkie, B. N. (1988) in *Can. J. Vet. Res.* 52:30–36. These culture supernatants, however, contain various soluble surface antigens of the bacterium and produce variable results when administered to animals. Other preparations include capsular extracts obtained via sodium salicylate extraction (see. e.g., Donanchie et al. (1984) 130:1209–1216; U.S. Pat. No. 4,346,074), saline extracted antigens (see, e.g., Lessley et al. (1985) *Veterinary Immunology and Immunopathology* 10:279–296; Himmel et al. (1982) *Am. J. Vet. Res.* 43:764–767), and modified live Pasteurella mutants.

Still other attempts at immunization have included the use of a purified cytotoxin from *P. haemolytica*. See, e.g. Gentry et al. (1985) *Vet. Immunology and Immunopathology* 9:239–250. This cytotoxin, which is a leukotoxin, is secreted by actively growing bacteria. Shewen, P. E., and Wilkie, B. N. (1987) *Infect. Immun.* 55:3233–3236. The gene encoding this leukotoxin has been cloned and expressed in bacterial cells. Lo et al. (1985) *Infect. Immun.* 50:667–671. Calves which survive *P. haemolytica* infections possess toxin-neutralizing antibody. Cho, H. J., and Jericho, K. W. F. (1986) *Can. J. Vet. Res.* 50:27–31; Cho et al. (1984) *Can. J. Comp. Med.* 48:151–155.

Cytokines are a group of hormone-like mediators produced by leukocytes. Cytokines serve as endogenous signals that act in conjunction with antigens to amplify both localized and systemic host defense mechanisms involving macrophages, lymphocytes, and other cell types. Representative lympokines include interleukin-1 (IL1), interleukin-2 (IL2), interleukin-3 (IL3), interleukin-4 (IL4), and gamma-interferon (gamma-IFN).

IL1 and IL2 both exhibit thymocyte mitogenic activity and IL2 stimulates T lymphocyte proliferation. IL3 stimulates the growth of hematopoietic progenitor cells and multipotential stem cells, and IL4 acts as an induction factor on resting B cells and as a B cell growth and differentiation factor. IL4 also exhibits T cell stimulatory activity.

Gamma-IFN is predominantly produced by antigen or mitogen-stimulated T lymphocytes. Gamma-IFN has been shown to be a potent immunomodulator and appears to enhance natural killer cell activity, antibody-dependent cellular cytotoxicity, and cytotoxic T lymphocyte activity (Lawman et al. (1989) "Recombinant Cytokines and their Potential Therapeutic Value in Veterinary Medicine" in Comprehensive Biotech, First Supplement, Animal Biotechnology, Pages 63–106 (Pergamon Press, London).

Gene fusions provide a convenient method for the production of chimeric proteins. The expression of chimeric proteins, such as a cytokine linked to an antigenic polypeptide, allows the simultaneous delivery of both agents to a desired recipient. PCT Publication No. WO 88/00971 (publication date of 11 Feb. 1988) describes the fusion of an IL2 gene with the influenza hemagglutinin coding sequence and the subsequent administration of the fusion protein using a viral vector. The application nowhere contemplates the use of a cytokine fused to leukotoxin for the treatment of pneumonia in animals.

DISCLOSURE OF THE INVENTION

The present invention is based on the construction of a novel gene fusion between the sequence encoding bovine IL2 and the *P. haemolytica* leukotoxin gene. These constructs produce a fusion protein that can be used to protect cattle and other animals from respiratory diseases such as pneumonia, including shipping fever pneumonia.

In one embodiment, the present invention is directed to a DNA construct comprising a first nucleotide sequence encoding a cytokine, or an active fragment thereof, operably linked to a second nucleotide sequence encoding at least one epitope of leukotoxin. In particularly preferred embodiments, the first nucleotide sequence encodes IL2, or an active fragment thereof.

In another embodiment, the subject invention is directed to expression cassettes comprised of (a) the DNA constructs above and (b) control sequences that direct the transcription of the construct whereby the constructs can be transcribed and translated in a host cell.

In yet another embodiment, the instant invention is directed to expression plasmid pAA356 (ATCC no. 68386).

In another embodiment, the invention is directed to host cells transformed with these expression cassettes.

Another embodiment of the invention provides a method of producing a recombinant polypeptide comprising (a) providing a population of host cells described above and (b) growing the population of cells under conditions whereby the polypeptide encoded by the expression cassette is expressed.

In still another embodiment, the invention is directed to an immunogenic chimeric protein comprising a cytokine, or an active fragment thereof, linked to at least one epitope of leukotoxin. In particularly preferred embodiments, the cytokine is derived from bovine IL2.

Also disclosed are vaccine compositions comprising the chimeric proteins and a pharmaceutically acceptable vehicle and methods of vaccinating a subject using the same.

These and other embodiments of the present invention will readily occur to those of ordinary skill in the art in view of the disclosure herein.

BRIEF DESCRIPTION OF THE FIGURES

FIG. 2 shows the structure of Plasmid pAA356 carrying a bovine IL2-leukotoxin (IL2-LKT) gene fusion wherein tac is the hybrid trp::lac promoter from *E. coli*; bla represents the β-lactamase gene (ampicillin resistance); lktA is the *P. haemolytica* leukotoxin structural gene; IL2 is the bovine interleukin-2 structural gene; and lac1 is the *E. coli* lac operon repressor.

FIGS. 3A-3K is the nucleotide sequence and predicted amino acid sequence of the bovine IL2-LKT chimeric protein from pAA356.

DETAILED DESCRIPTION

Figure 1:
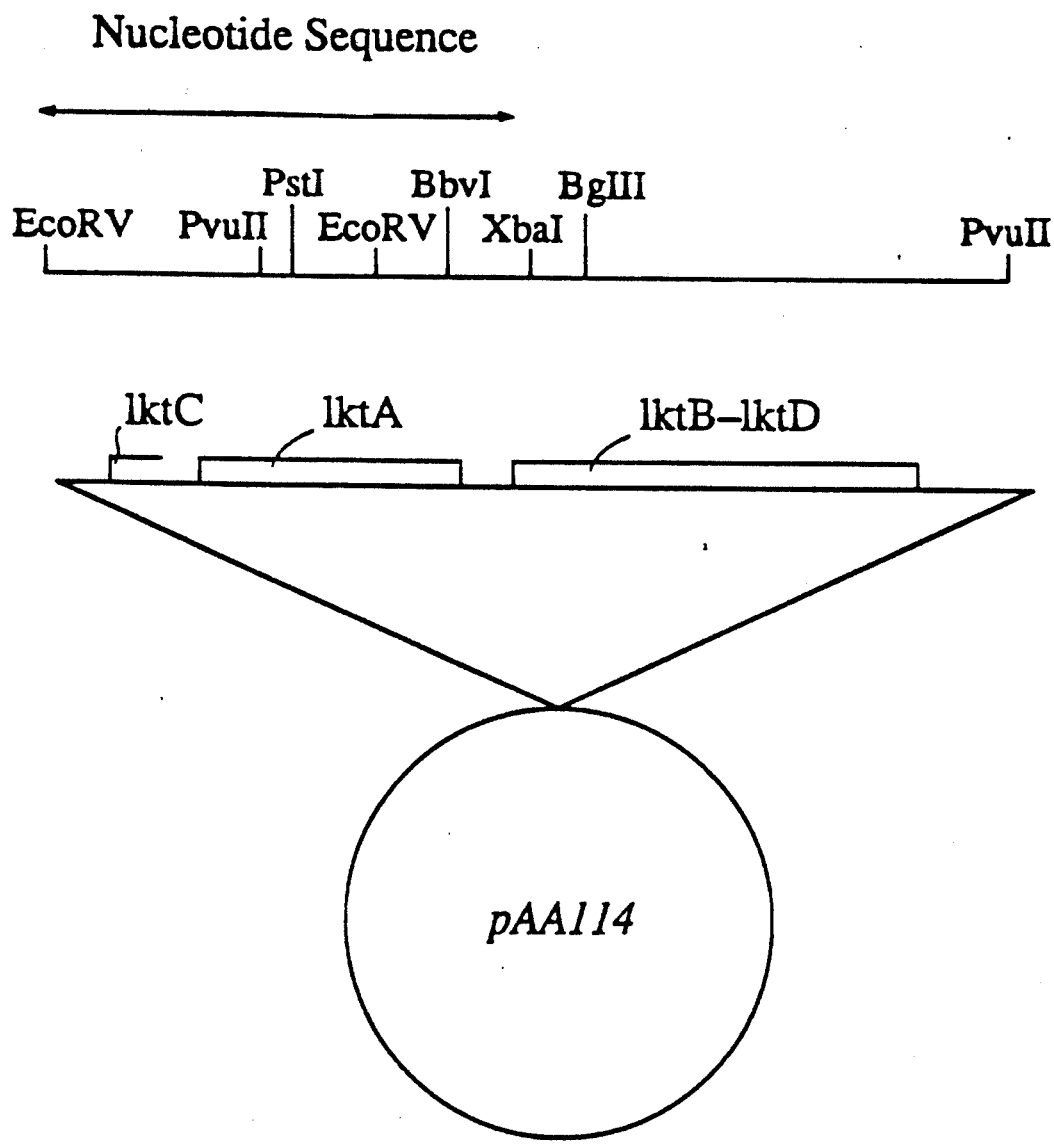
FIG. 1 depicts the structure of the leukotoxin gene of *P. haemolytica* cloned in *E. coli* (Plasmid pAA114).

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); B. Perbal, *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

A. Definitions

In describing the present invention, the following terms will be employed, and are intended to be defined as indicated below.

By "cytokine" is meant any one of the group of hormone-like mediators produced by T and B lymphocytes. Representative cytokines include but are not limited to IL1, IL2, IL3, IL4 and gamma-IFN. An "active" fragment of a cytokine is a fragment of a cytokine which imparts proliferative activity to the subject fusion proteins as measured in standard assays, such as the cell proliferation assay described in the experimental section below.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

An "immunogenic polypeptide" or "immunogenic amino acid sequence" is a polypeptide or amino acid sequence, respectively, which elicits an immunological response in a subject to which it is administered.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from a source occurring in nature. Thus, the term "native leukotoxin" would include naturally occurring leukotoxin and fragments thereof.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "rotavirus VP6 protein" refers to the art recognized major viral protein of the inner capsid from any species or strain within the family Reoviridae. See, e.g., Kapikian et al., 1985. Examples of rotavirus strains from which the VP6 protein can be isolated and employed in the present invention include, but are not limited to, Simian SA-11, human D rotavirus, bovine UK rotavirus, human Wa or W rotavirus, human DS-1 rotavirus, rhesus rotavirus, the "O" agent, bovine NCDV rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU-1 rotavirus, feline Taka rotavirus, equine H-2 rotavirus, human St. Thomas No. 3 and No. 4 rotaviruses, human Hosokawa rotavirus, human Hochi rotavirus, porcine SB-2 rotavirus, porcine Gottfried rotavirus, porcine SB-1A rotavirus, porcine OSU rotavirus, equine H-1 rotavirus, chicken Ch.2 rotavirus, turkey Ty.1 rotavirus, bovine C486 rotavirus, and strains derived from them. Thus the present invention encompasses the use of VP6 from any rotavirus strain, whether from subgroup I, subgroup II, or any as yet unidentified subgroup, as well as from any of the serotypes 1-7, as well as any as yet unidentified serotypes. Such VP6 proteins can be used as immunologic carriers of polypeptides. These carrier molecules comprise amino acid sequences of rotavirus VP6 amino acid sequences which are unique to the class, or any member of the class, of VP6 polypeptides. Such unique sequences of VP6 proteins are referred to as a "rotavirus VP6 inner capsid protein amino acid sequence."

A carrier that is "substantially homologous to a rotavirus VP6 inner capsid protein or a functional fragment thereof" is one in which at least about 85%, preferably at least about 90%, and most preferably at least about 95%, of the amino acids match over a defined length of the molecule. A "functional fragment" of a rotavirus VP6 inner capsid protein is a fragment with the capability of acting as a carrier molecule for the novel chimeric proteins of the instant invention.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" or a "nucleotide sequence encoding" a particular protein, is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the $-10$ and $-35$ consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" another coding sequence when RNA polymerase will transcribe the two coding sequences into mRNA, which is then translated into a chimeric polypeptide encoded by the two coding sequences. The coding sequences need not be contiguous to one another so long as the transcribed sequence is ultimately processed to produce the desired chimeric protein.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 80% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The term "functionally equivalent" intends that the amino acid sequence of the subject fusion protein is one that will elicit an immunological response, as defined above, equivalent to an immunogenic IL2-LKT chimeric protein.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A +B in the composition, more preferably at least about 95%, or even 99% by weight.

The term "treatment" as used herein refers to either (i) the prevention of infection or reinfection (prophylaxis), or (ii) the reduction or elimination of symptoms or the disease of interest (therapy).

B. General Methods

Central to the instant invention is the production of a chimeric protein comprising a cytokine and a *P. haemolytica* leukotoxin. This chimeric protein can be used in a vaccine composition to protect animals against respiratory diseases such as pneumonia, including shipping fever pneumonia.

Actively growing cells of *P. haemolytica* have been shown to secrete leukotoxin which can be cloned, the gene encoding the same isolated, and fused with a gene encoding an appropriate cytokine, using techniques well known in the art. The resulting chimeric proteins can be expressed and used to immunize subjects against shipping fever.

The nucleotide sequence coding for *P. haemolytica* A1 leukotoxin has been determined. See, e.g., Lo, R. Y. C. (1987) *Infect. Immun.* 55:1987–1996. Of interest is the fact that the *P. haemolytica* leukotoxin gene and the corresponding protein share extensive homology with *Escherichia coli* alpha hemolysin (50.3% of the amino acid residues are identical). Strathdee, C. A., and Lo, R. Y. C. (1987) *Infect. Immun.* 55:3233–3236. *P. haemolytica* leukotoxin can be produced using recombinant techniques and purified from, for example, bacterial cells. The leukotoxin can also be purified from native bacteria using immunoadsorbent chromatography. The molecular weight of the purified leukotoxin is approximately 95,000 and the isoelectric point is 6.3.

Similarly, the coding sequences for numerous cytokines have been elucidated. See, e.g., Maliszewski et al. (1988) *Molec. Immun.* 25:429–437 and Ceretti et al. (1986) *Proc. Natl. Acad. Sci.*, U.S.A. 83:2332–2337. Again, these cytokines can be purified using standard techniques.

Purification of the above proteins as described herein permits the sequencing of the same by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art. Furthermore, fragments of the proteins can be tested for biological activity and active fragments used in compositions in lieu of the entire protein.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; T. Maniatis et al., supra.

First, a DNA library is prepared. The library can consist of a genomic DNA library from *P. haemolytica* (for the isolation of the leukotoxin gene) or from appropriate T cells (for the isolation of the desired cytokine gene). Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; T. Maniatis et al., supra; B. Perbal, supra.

Suitable restriction enzymes can then be employed to isolate the appropriate cytokine gene or leukotoxin gene and these sequences can be ligated together and cloned to form a cytokine-leukotoxin fusion gene.

The fusion gene can be placed under the control of a promoter, ribosome binding site (for bacterial expression) and, optionally, an operator (collectively referred to herein as "control" elements), so that the DNA sequence encoding the chimeric protein is transcribed into RNA in the host cell transformed by a vector containing this expression construction. The coding sequence may or may not contain a signal peptide or leader sequence. The chimeric proteins of the present invention can be expressed using, for example, native *P. haemolytica* promoter, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular fusion coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular chimeric protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the chimeric proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The chimeric protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired antigen.

The chimeric proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Animals can be immunized with the compositions of the present invention by administration of the chimeric protein, or a fragment thereof, or an analog thereof. The chimeric protein can consist of an epitope of leukotoxin fused to an active fragment of a cytokine, as defined above. Thus, if the fragment or analog of the fusion protein is used, it will include the amino acid sequence of an epitope of leukotoxin which interacts with the immune system to immunize the animal to that and structurally similar epitopes, and an active fragment of a cytokine as defined above.

Chimeric proteins used to immunize a subject contain at least 6–30 amino acids which form the sequence of the desired chimeric protein, and include a leukotoxin epitope and an active cytokine fragment.

Prior to immunization, it may be desirable to increase the immunogenicity of the particular chimeric protein, or an analog of the protein, or particularly fragments of the protein. This can be accomplished in any one of several ways known to those of skill in the art. For example, the antigenic peptide may be administered linked to a carrier. For example, a fragment may be conjugated with a macromolecular carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the chimeric proteins of the present invention include VP6 polypeptides of rotaviruses, or functional fragments thereof, as disclosed in U.S. Pat. No. 5,071,651, and incorporated herein by reference. Also useful is a fusion product of a viral protein and the subject cytokine-leukotoxin immunogen made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the fusion proteins of the present invention may be coupled to erythrocytes, preferably the subject's own erythrocytes. Methods of coupling peptides to proteins or cells are known to those of skill in the art.

The novel chimeric proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel chimeric proteins can be constructed as follows. The DNA encoding the particular cytokine-leukotoxin chimeric protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant chimeric protein into the viral genome. The resulting TK$^-$ recombinant can be selected by culturing the cells in the presence of 5-bromodeoxyuridine and picking viral plaques resistant thereto.

It is also possible to immunize a subject with a protein of the present invention, or a protective fragment thereof, or an analog thereof, which is administered alone, or mixed with a pharmaceutically acceptable vehicle or excipient. Typically, vaccines are prepared as injectables, either as liquid solutions or suspensions;

solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th edition, 1975. The composition or formulation to be administered will, in any event, contain a quantity of the protein adequate to achieve the desired immunized state in the individual being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the chimeric protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The chimeric proteins can also be delivered using implanted minipumps, well known in the art.

Furthermore, the chimeric proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, the polypeptide of interest, or an immunologically active fragment thereof, is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. With the present vaccine formulations, 50 ug of active ingredient per ml of injected solution should be adequate to raise an immunological response when a dose of 1 to 5 ml per animal is administered. Other effective dosages can be readily established by one of ordinary skill in the art through routine trials establishing dose response curves. The subject is immunized by administration of the particular antigen or fragment thereof, or analog thereof, in at least one dose, and preferably two doses. Moreover, the animal may be administered as many doses as is required to maintain a state of immunity to pneumonia.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

| Strain | Deposit Date | ATCC No. |
| --- | --- | --- |
| P. haemolytica serotype 1 B122 | February 1, 1989 | 53863 |
| pAA356 in E. coli W1485 | August 14, 1990 | 68386 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T_4$ DNA ligase, *E. coli*, DNA polymerase I, Klenow fragment, and other biological reagents were purchased from commercial suppliers and used according to the manufacturers' directions. Double-stranded DNA fragments were separated on agarose gels.

cDNA and genomic libraries were prepared by standard techniques in pUC13 and the bacteriophage lambda gt1, respectively. See DNA CLONING: Vols I and II, supra.

*P. haemolytica* biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

EXAMPLE 1

Construction of an IL2-leukotoxin Gene Fusion

1. Modification of the Bovine IL2 Gene

The bovine IL2 gene, in the plasmid pBOVIL2, (CIBA-GEIGY, Basel, Switzerland) was digested to completion with the restriction endonuclease BclI and the single-stranded ends removed by Mung Bean nuclease treatment. The DNA was then digested with EcoRI in order to excise the IL2 gene fragment. This fragment was ligated into the cloning vector pTZ19R (Pharmacia, Canada) (EcoRI/SmaI-digested). Sequence analysis revealed two populations of clones which differed only in the reading frame at the 3'-end of the gene. The first, pAA284, had a terminal sequence of 5'-TCA ACA ATG ACT GGG ATC CTC-3' (BamHI site in vector underlined) while the second, pAA285, had a terminal sequence of 5'-TCA ACA ATG ACT GGG GAT CCT-3'. The sequences shown in bold face are from the IL2 gene. Because of the differences in reading frame, heterologous genes in two out of three reading frames can be fused to the bovine IL2 gene.

2. Construction of IL2-LKT Fusions

To isolate the leukotoxin gene, gene libraries of *P. haemolytica* A1 (strain B122) were constructed using standard techniques. See Lo et al., *Infect. Immun.*, supra; *DNA CLONING: Vols. I and II*, supra; and T. MANIATIS et al., supra. A genomic library was constructed in the plasmid vector pUC13 and a DNA library constructed in the bacteriophage lambda gt11. The resulting clones were used to transform *E. coli* and individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See Lo et al., *Infect. Immun.*, supra. To confirm this, smaller fragments were recloned and the restriction maps compared. It was determined that approximately 4 kilobase pairs of DNA had been cloned. Progressively larger clones were isolated by carrying out a chromosome walk (5' to 3' direction) in order to isolate full-length recombinants which were approximately 8 kb in length. The final construct was termed pAA114. This construct contained the entire leukotoxin gene sequence. The structure of this plasmid is shown in FIG. 1.

lktA, a MaeI restriction endonuclease fragment from pAA114 which contained the entire leukotoxin gene, was treated with the Klenow fragment of DNA polymerase I plus nucleotide triphosphates and ligated into the SmaI site of the cloning vector pUC13. This plasmid was named pAA179. From this, an expression construct was made in the ptac-based vector pGH432: lacI digested with SmaI. This construct was termed pAA345 and contained the entire MaeI fragment described above. This plasmid expresses full-length leukotoxin.

The plasmid pAA345 containing the *P. haemolytica* leukotoxin gene lktA was digested with BamHI and BglII, and the 2.75 kilobase fragment was ligated into BamHI-digested pAA285 (above). The resulting plasmid, pAA354, was digested with ApaLI, the 5'-overhang filled in with the Klenow fragment of DNA polymerase I, and finally digested with BamHI. The IL2-LKT fragment was gel purified and ligated into the expression vector pGH433 lacI which had been cut with BglII, filled in with Klenow polymerse and digested with BamHI. The resulting clone, pAA356 (ATCC No. 68386), contained the desired gene fusion under the control of the *E. coli* tac promoter. FIG. 2 shows the structure of pAA356 while FIG. 3 shows the nucleotide sequence and corresponding amino acid sequence of the fusion protein expressed by this plasmid. The resulting fusion is a gene fusion of bovine IL2 to the 5'-end of the 1ktA gene (approximately 750 bp).

EXAMPLE 2

Measurement of IL2 Activity

Cell-free lysates were prepared by detergent lysis from *E. coli* carrying pAA356 and an isogenic strain carrying the pGH433 vector without IL2-LKT. The IL2-LKT molecule was evident on polyacrylamide gel electrophoresis. IL2 activity was measured using an IL2-dependent T-cell line derived from concanavalin-A-stimulated peripheral blood mononuclear cells. The recombinant lysates were added to IL2-dependent cells and proliferation was measured after 48 hours incubation at 37° C. The proliferative response to IL2 was compared to T lymphocytes cultured in medium alone or cells stimulated with recombinant human IL2 (specific activity $=3.6\times10^6$ U/mg). Recombinant leukotoxin without IL2 was also included as a control. The results, shown in Table 1, confirm the IL2 activity of the fusion protein.

TABLE 1

IL2 Activity of IL2-LKT Fusion Product
Tested on an IL2-Dependent T-Cell Line[a]

| Sample | Counts per Minute | | |
|---|---|---|---|
| | $10^{-2}$ | $10^{-3}$ | $10^{-4}$ |
| Recombinant Leukotoxin | 357 | 372 | 383 |
| Vector Only (pGH433) | 487 | 598 | 506 |
| IL2-LKT (pAA356) | 28,634 | 22,329 | 9,961 |

[a]Activity induced by recombinant human IL2 standards:
25 U/ml = 30,159 cpm; 12 U/ml = 23,666 cpm; 6 U/ml = 22,837 cpm; 3 U/ml = 15,828 cpm; 1.5 U/ml = 8,944 cpm; 0.6 U/ml = 3,233 cpm.

Thus, it is evident that the chimeric protein retains IL2 cell proliferation activity.

EXAMPLE 3

Serological Response to *P. haemolytica* LKT and the IL2-LKT Chimeric Molecule

To test whether the serological activity of the chimeric molecule differed from the serological activity of leukotoxin alone, the following experiment was done.

Calves (three per group) were immunized at time 0 with 100 μg of: (1) full-length recombinant *P. haemolytica* leukotoxin (LKT), (2) an equivalent molar ratio of the IL2-LKT chimeric protein, or (3) PBS. All of these were formulated in phosphate-buffered saline with Emulsigen as the adjuvant. Serological assessment of immune responsiveness to LKT or the chimera was carried out at −15, −7, −3 days and immediately prior to immunization on day 0, and daily for 20 days postimmunization. Serum antibody of the IgG class was assessed by enzyme-linked immunosorbent assay, using leukotoxin as the antigen.

Figure 4A:
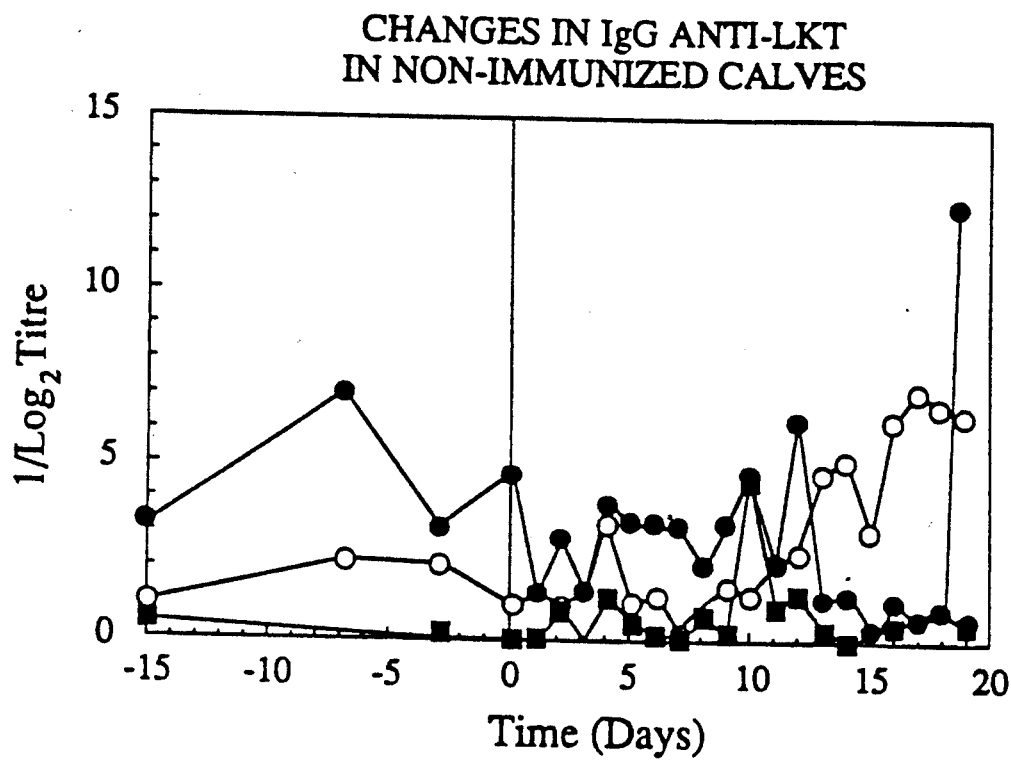
FIGS. 4A-4C depicts the changes in IgG anti-LKT in nonimmunized calves (FIG. 4A), LKT-immunized calves (FIG. 4B), and calves immunized with an IL2-LKT fusion protein (FIG. 4C).
Figure 4B:
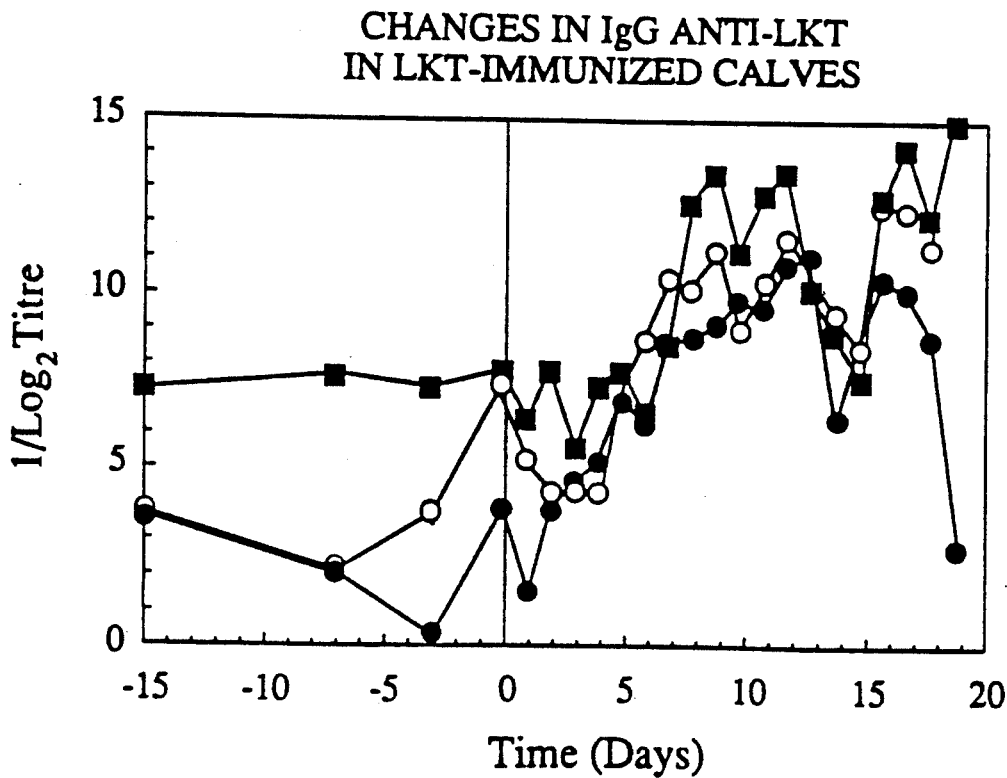
Figure 4C:
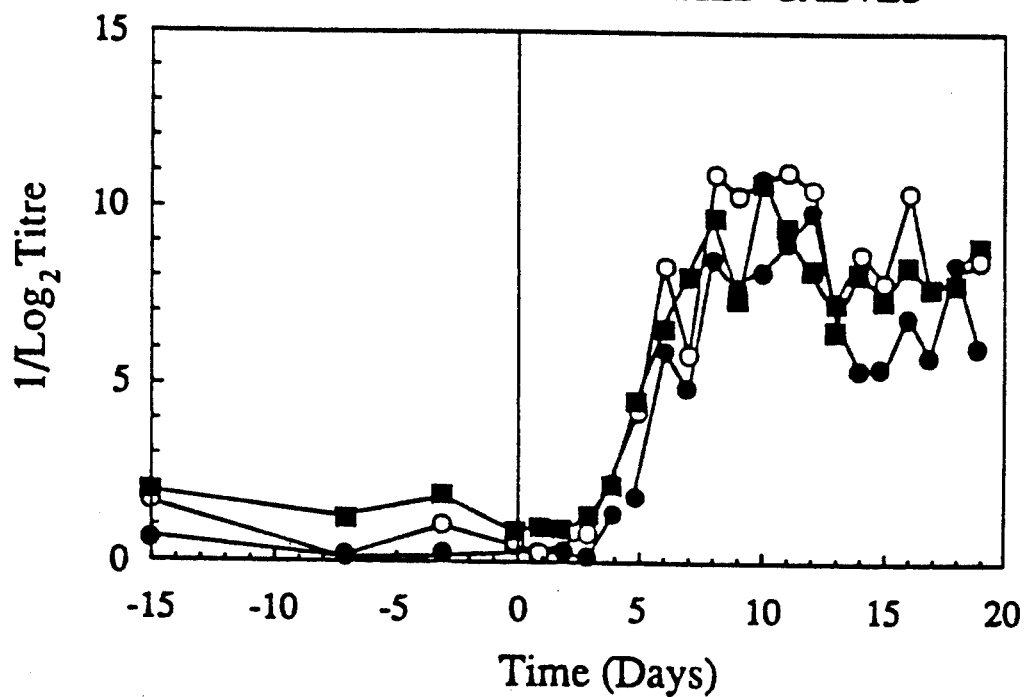

As can be seen in FIGS. 4A–4C, the mean of individual serological titers in the nonimmunized group (FIG. 4A) remained at levels below 1/32 ($log_2 5$). One of the three calves in this group seroconverted to leukotoxin positive at day 20 because of natural infection with *P. haemolytica*. In the LKT-immunized group (4B), titers began to rise at day 6 after immunization, reaching a maximum (1/1024–1/8192; $log_2$ 10–14) on day 8–10, where they remained for the duration of the experiment. In the chimera-immunized animals (4C), responses to LKT began to rise after day 4 postimmunization, reaching a maximum (1/1024–1/4096 $log_2$ 10–12) on day 8 after immunization.

Thus, the serological activity of the chimeric molecule when compared to the activity of leukotoxin alone was not significantly different, both with respect to kinetics and magnitude. Serum antibody from one animal in the leukotoxin immunized group appeared to react with leukotoxin prior to immunization (with titers >1/128; $log_2$ 7), and while it is unlikely that this animal suffered a *P. haemolytica* infection, serum antibodies against another bacterial toxin could be cross-reacting with leukotoxin. The conclusion from this experiment is that when IL2 is genetically chimerized to the leukotoxin molecule, it does not affect the ability of the LKT to induce a normal IgG antibody response when compared to the administration of recombinant leukotoxin alone.

EXAMPLE 4

Immunization of Calves with LKT and the IL2-LKT Chimeric Molecule

Calves were immunized at time 0 according to the protocols in Table 2. 117 micrograms of IL2-LKT were given (molar equivalent) and 100 micrograms of LKT given (molar equivalent).

TABLE 2

Calf Immunization Protocols

| Antigen | Adjuvant | Number of Doses | Interval |
|---|---|---|---|
| LKT | Emulsigen-plus | 5 | 12 H |
| IL2-LKT | Emulsigen-plus | 5 | 12 H |
| IL2-LKT | Emulsigen-plus | 1 | |
| IL2-LKT | None | 5 | 12 H |

LKT refers to full-length leukotoxin.
IL2-LKT refers to LKT chimerized to bovine IL2.
In multiple-dose regimes, five doses were given at 12 h intervals over 2.5 days.

1. Precursor Frequency Analysis.

The number of cells capable of responding to LKT following immunization was assessed using limiting dilution analysis (LDA). At the times indicated following immunization, T and B lymphocytes were isolated from peripheral blood by passing through Sephadex G-10 columns. Monocyte depletion was confirmed by flow cytometry. This cell population was diluted to various concentrations ($10^5$ to $10^2$/ml) and added to 96-well plates in the presence of feeder cells (autologous 1500 rad irradiated PBMC) and antigen (LKT) at a previously determined optimal concentration (20 μg/ml). In some experiments, cells were stimulated with IL2-LKT (LKT356) or an equimolar concentration of IL2. Following incubation at 37° C. for 5 to 7 days, $^3$H-thymidine was added to wells and cultures were harvested after an additional 24 hours incubation, counted and the percent negative cultures assessed following comparison with control cultures (i.e., cells cultured in the absence of antigen). Semi-$Log_{10}$ plots were done of $Log_{10}$ Percent negative cultures (Y) against number of cells plated (X). The number of cells responding at 37% negative cultures was calculated from an equation derived from the regression curve of Y versus X.

Figure 5:
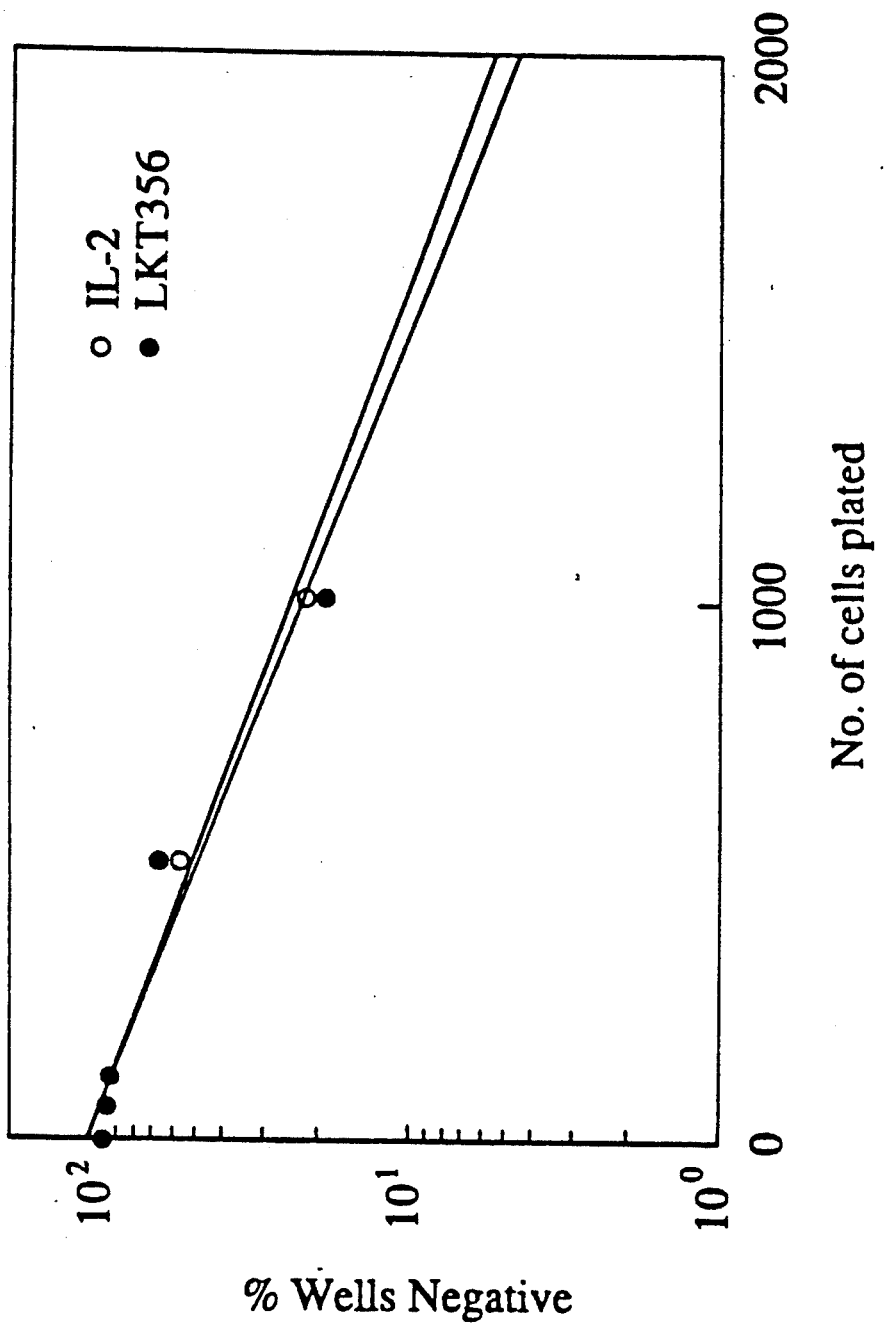
FIG. 5 shows precursor frequency analysis of PBMC responding to recombinant bovine IL2-LKT chimeric protein.

As can be seen in FIG. 5, the chimerization of LKT to IL2 does not affect the ability of PBMC to respond to the IL2 component of the molecule. Furthermore, precursor frequency analysis of cells responding to LKT or IL2-LKT yielded the following results: After immunization with LKT or IL2-LKT, with or without the adjuvant Emulsigen-plus, there was a dramatic increase in the number of cells responding to LKT. Following a single immunizing dose of IL2-LKT with Emulsigen-plus, there was no detectable increase in precursor frequency (Table 3).

Serology

Serum from the immunized calves was assessed for antibodies against LKT at the times indicated in Table 3. LKT antibodies were detected using standard ELISAs.

All animals showed an increased antibody titer against LKT following immunization. Increases were more marked in those animals given Emulsigen-plus in the formulation. Specifically, animals immunized with the chimera had a titer of 1/700 15 days after immunization, whereas when the same immunization was done with Emulsigen-plus, the titer was 1/35,000. Furthermore, even following one dose of IL2-LKT with Emulsigen-plus, the serological titer was 1/2500 (Table 3).

TABLE 3

| Immunization[a] | Adjuvant[b] | Time (D)[c] | F[d] | Serology[e] |
|---|---|---|---|---|
| LKT (M) | Emulsigen-plus | 0 | 1:55657 | 1/150 |
|  |  | 15 | 1:11087 | 1/6000 |
| IL2-LKT (M) | None | 0 | 1:16728 | 1/200 |
|  |  | 15 | 1:8976 | 1/700 |
| IL2-LKT (S) | Emulsigen-plus | 0 | 1:50755 | 1/300 |
|  |  | 15 | 1:117317 | 1/2500 |
| IL2-LKT (M) | None*** | 0 | 1:20728 | 1/1000 |
|  |  | 15 | 1:16882 | 1/35000 |

[a]M: multiple dose regimen; S: single bolus dose.
[b]Adjuvant given with all doses. ***High values at time 0 may indicate a prior infection or x-reactivity.
[c]Time following first inoculation.
[d]Precursor frequency of B and T cells proliferating in response to LKT.
[e]Serology determined by ELISA using LKT as antigen.

Thus, this study demonstrated the ability of LKT and IL2-LKT formulations to elicit cellular and humoral immunity responses following single or multiple immunization. When Emulsigen-plus was used as an adjuvant, there was a high serological response. This was regardless of whether LKT or IL2-LKT was given as a single or multiple immunization regimen. The single dose inoculum gave a high humoral response (antibody titer) in the near absence of any detectable cellular response. The animal that elicited the highest cellular response after immunization was that which was given IL2-LKT alone. Thus, IL2-LKT can elicit the highest state of cellular reactivity. A higher humoral response can also be elicited by combining the chimeric protein with an adjuvant.

EXAMPLE 5

Identification of Neutralizing Epitopes of Leukotoxin

The *P. haemolytica* leukotoxin protein contains a series of repeated amino acid domains near the carboxy terminus. These domains are likely to be epitopes useful in the subject chimeric proteins. The consensus amino acid sequence is Gly-Gly-X-Gly-X-Asp, where X is Lys, Asp, Val or Asn. (Highlander et al. (1989) *DNA* 8:15–28.) However, other substitutions likely to render immunologically active peptides include substitutions with an aliphatic amino acid, such as Gly, Ala, Val, Leu, Ile, a charged amino acid such as Asp, Glu, Arg, His or Lys, or a corresponding neutral amino acid such as Asn or Gln.

Based on this information, a synthetic peptide of the sequence GGNGDDFIDGGKGNDLLHGG was constructed by standard solid phase technology on an Applied Biosystems peptide synthesizer. Mice were immunized with authentic leukotoxins prepared from either *P. haemolytica*, or *Actinobacillus pleuropneumoniae* (serotypes 1 and 5) at 100 micrograms per dose with Freund's Complete Adjuvant (first vaccination) or Freund's Incomplete Adjuvant (all subsequent vaccinations). High titer serum samples from immunized mice were tested, in a standard ELISA, for the following: (1) their ability to react with recombinant and authentic *P. haemolytica* leukotoxin; (2) their ability to react with the toxin produced by *A. pleuropneumoniae*; and (3) their ability to react with the synthetic peptide described above. The results, summarized in Table 2, are expressed as the relative reactivity at a serum dilution of 1 in 100,000.

TABLE 4

Presence of Synthetic Peptide Epitopes in Toxins from *P. haemolytica* and *A. pleuropneumonia* serotypes 1 and 5

| Toxin Prepared From: | Relative Serological Response To: | | |
|---|---|---|---|
|  | Synthetic Peptide | Actinobacillus Toxin | Pasteurella Toxin |
| *A. pleuropneumoniae* sero. 5 | +++ | ++++ | ++ |
| *A. pleuropneumoniae* sero. 1 | + | ++++ | + |
| *P. haemolytica* | +++ | not determined | ++++ |

This data indicated that animals vaccinated with either of the three leukotoxins developed antibodies which reacted with all toxins and a synthetic peptide based on a portion of the *P. haemolytica* toxin. Once an appropriate level of anti-peptide serum antibody was reached (ELISA titer of 100,000 or greater), spleen cells were fused with NS1 cells and monoclonal antibody-producing clones were isolated by standard techniques. Culture supernatants from these clones were tested for their ability to react with the synthetic peptide (above) and the respective toxins in an ELISA assay. The results for 2 clones are shown in Table 5.

TABLE 5

| Clone | Immunogen | Relative Reaction With: | | |
|---|---|---|---|---|
|  |  | Pasteurella Toxin | Synthetic Peptide | Actinobacillus Toxin |
| ET122-6A4-3 | Pasteurella toxin | ++++ | +++++ | ND[1] |
| N37-3F9-6 | Actinobacillus toxin | ND | ++++ | +++++ |

[1]Not determined

These results demonstrate that each of these monoclonal antibodies react with an epitope which is shared by the *P. haemolytica* and *A. plauropneumoniae* toxins, and that this epitope is structurally similar to that of the synthetic peptide. This peptide is also structurally similar to a bovine rotavirus synthetic peptide of the sequence TMNGNEFQTGGIGNLPIRNWNAC, representing amino acids 40–60 of the VP6 protein. The monoclonal antibodies described above can therefore be used to determine the degree of their cross-reactivity with rotavirus proteins based on the epitope represented by the synthetic peptides. Furthermore, the immunologically active leukotoxin fragments might prove useful in immunizing against rotavirus.

These leukotoxin epitopes can be fused to cytokines such as IL2, or active fragments thereof, to form chimeric proteins for use in vaccine compositions.

Thus, chimeric proteins for use in stimulating immunity against pneumonia and other respiratory diseases have been disclosed. Although preferred embodiments of the subject invention have been described in some detail, it is understood that obvious variations can be made without departing from the spirit and the scope of the invention as defined by the appended claims.

We claim:

1. A DNA construct comprising a first nucleotide sequence encoding interleukin-2 (IL-2), operably linked to a second nucleotide sequence encoding a leukotoxin, wherein said leukotoxin is characterized by having the amino acid sequence G-G-X-G-X-D, where X is K, D, V or N.

2. The DNA construct of claim 1 wherein said IL-2 is bovine IL-2.

3. The DNA construct of claim 2 comprising the nucleotide sequence in FIG. 3.

4. The DNA construct of claim 1 wherein said nucleotide sequence encoding IL-2 is linked to the 5'-end of said nucleotide sequence encoding leukotoxin.

5. The DNA construct of claim 1 wherein said leukotoxin is *P. haemolytica* leukotoxin.

6. An exprssion vector comprised of:

(a) the DNA construct of claim 1; and (b) control sequences operably linked to said DNA construct that direct the transcription of said construct whereby said construct can be transcribed and translated in a host cell.

7. An expression vector comprised of:

(a) the DNA construct of claim 3; and (b) control sequences operably linked to said DNA construct that direct the transcription of said construct whereby said construct can be transcribed and translated in a host cell.

8. Plasmid pAA356 (ATCC no. 68386).

9. A host cell stably transformed with the expression vector of claim 6.

10. A host cell stably transformed with the expression vector of claim 7.

11. A host cell stably transformed with the plasmid of claim 8.

12. A method of producing a recombinant polypeptide comprising:

(a) culturing a population of cells according to claim 9 under conditions whereby the polypeptide encoded by said expression vector is expressed; and (b) isolating the expressed polypeptide.

13. A method of producing a recombinant polypeptide comprising:

(a) culturing a population of cells according to claim 10 under conditions whereby the polypeptide encoded by said expression vector is expressed; and (b) isolating the expressed polypeptide.

14. A method of producing a recombinant polypeptide comprising:

(a) culturing a population of cells according to claim 11 under conditions whereby the polypeptide encoded by said expression vector is expressed; and (b) isolating the expressed polypeptide.

* * * * *